(12) United States Patent
Tsuboi et al.

(10) Patent No.: US 8,510,063 B2
(45) Date of Patent: Aug. 13, 2013

(54) CONTROL DEVICE, CONTROL METHOD, AND PROGRAM

(75) Inventors: Toshimitsu Tsuboi, Tokyo (JP); Takeo Kishida, Osaka (JP)

(73) Assignee: Sony Corporation, Tokyo (JP)

( * ) Notice: Subject to any disclaimer, the term of this patent is extended or adjusted under 35 U.S.C. 154(b) by 892 days.

(21) Appl. No.: 12/621,205

(22) Filed: Nov. 18, 2009

(65) Prior Publication Data

US 2010/0125423 A1 May 20, 2010

(30) Foreign Application Priority Data

Nov. 19, 2008 (JP) .................................. 2008-295360

(51) Int. Cl.
*A61B 5/22* (2006.01)
(52) U.S. Cl.
USPC ............................................. 702/41; 73/841
(58) Field of Classification Search
USPC .................... 702/41, 43, 170; 700/245, 258, 700/260, 261; 73/841
See application file for complete search history.

(56) References Cited

U.S. PATENT DOCUMENTS

2010/0139418 A1* 6/2010 Loeb et al. ............... 73/862.046

FOREIGN PATENT DOCUMENTS

| JP | 57-052982 | 3/1982 |
| JP | 04-107795 | 4/1992 |
| JP | 2005-144573 | 6/2005 |

* cited by examiner

*Primary Examiner* — Manuel L Barbee
(74) *Attorney, Agent, or Firm* — Finnegan, Henderson, Farabow, Garrett & Dunner, LLP

(57) ABSTRACT

A control device includes a force detector configured to detect a force in a normal direction and a force in a shearing direction of fingertips of a robot hand device respectively as a normal force and a shearing force, and an object detector configured to calculate a friction coefficient using the normal force and the shearing force detected by the force detector and to detect whether or not a thin-film object having a maximum friction coefficient different from a maximum stationary friction coefficient between the fingertips is grasped between the fingertips on the basis of the calculation result.

5 Claims, 14 Drawing Sheets

CONTROL DEVICE, CONTROL METHOD, AND PROGRAM

BACKGROUND OF THE INVENTION

1. Field of the Invention

The present invention relates to control devices, control methods, and programs. In particular, the present invention relates to a control device, a control method, and a program that allow for accurate detection of whether a thin-film object is in a grasped state in a robot hand device.

2. Description of the Related Art

The following are two related-art examples of techniques for detecting the number of sheets of paper. The first technique is disclosed in Japanese Unexamined Patent Application Publication No. 57-52982 and involves nipping paper between two objects with a certain amount of force and sliding the two objects against each other in a direction parallel to the plane of the paper. By detecting whether or not the sliding force is greater than a predetermined value, it is determined whether there is one sheet of paper or there are more than two sheets of paper.

The second technique is disclosed in Japanese Unexamined Patent Application Publication No. 4-107795 and involves nipping paper with pressure using separation members coated with a reusable low-adhesion adhesive, releasing the pressure, and then sliding the separation members in a direction parallel to the contact plane of the paper. By detecting whether or not the sliding force is greater than a predetermined value, it is determined whether there is one sheet of paper or there are more than two sheets of paper.

As an example of a technique for detecting whether or not an object is grasped by fingertips (referred to as "grasp detection technique" hereinafter) in a robot hand device of the related art, there is a technique that employs a vision sensor for the grasp detection. Another example is a technique of detecting whether the fingertips are open using a position sensor such as a rotary encoder, detecting whether an object is in contact with the fingertips using, for example, a tactile sensor, such as a contact sensor, or a force sensor, and then detecting whether an object having a certain dimension is grasped.

SUMMARY OF THE INVENTION

However, the above-described first and second techniques of the related art used for determining the number of sheets of paper are based on the precondition that at least one sheet of paper is grasped, and it is therefore difficult to detect a non-grasped state of paper.

Furthermore, with the above-described grasp detection techniques of the related art, detection of a thin-film-like object (referred to as "thin-film object" hereinafter) is sometimes difficult even when a thin-film object is in a grasped state. For example, this applies to when it is difficult to detect that the fingertips are open using the aforementioned position sensor. This also applies to when it is too dark that the detection is difficult using the aforementioned vision sensor. Moreover, this also applies to when the thin-film object is too small that the thin-film object is hidden by the fingertips.

Other examples of grasp detection techniques of the related art include techniques that employ devices such as contact switches and photo-interrupters. These grasp detection techniques of the related art are based on the precondition that a thin-film object will pass the set position of these devices. Therefore, these grasp detection techniques of the related art are not suitable for a robot hand device that can move and rotate freely.

It is desirable to allow for the capability to accurately detect that a thin-film object is in a grasped state in a robot hand device.

A control device according to an embodiment of the present invention includes force detecting means for detecting a force in a normal direction and a force in a shearing direction of fingertips of a robot hand device respectively as a normal force and a shearing force, and object detecting means for calculating a friction coefficient using the normal force and the shearing force detected by the force detecting means and for detecting whether or not a thin-film object having a maximum friction coefficient different from a maximum stationary friction coefficient between the fingertips is grasped between the fingertips on the basis of the calculation result.

The control device may further include position detecting means for detecting a position of the fingertips. The object detecting means may further detect whether or not a non-thin-film object thicker than the thin-film object is grasped between the fingertips on the basis of the detection result of the position detecting means. If the detection result indicates that the non-thin-film object is grasped between the fingertips, the object detecting means may prohibit the detection of whether or not the thin-film object is grasped between the fingertips. If the detection result indicates that the non-thin-film object is not grasped between the fingertips, the object detecting means may commence the detection of whether or not the thin-film object is grasped between the fingertips.

The object detecting means may compare a threshold value preliminarily determined from the maximum stationary friction coefficient between the fingertips with the friction coefficient and detect whether or not the thin-film object is grasped between the fingertips on the basis of the comparison result.

A control method according to an embodiment of the present invention includes the steps of causing a control device to detect a force in a normal direction and a force in a shearing direction of fingertips of a robot hand device respectively as a normal force and a shearing force, and causing the control device to calculate a friction coefficient using the detected normal force and the detected shearing force and to detect whether or not a thin-film object having a maximum friction coefficient different from a maximum stationary friction coefficient between the fingertips is grasped between the fingertips on the basis of the calculation result.

A program according to an embodiment of the present invention executes a control process that includes the steps of causing a computer to detect a force in a normal direction and a force in a shearing direction of fingertips of a robot hand device respectively as a normal force and a shearing force, and causing the computer to calculate a friction coefficient using the detected normal force and the detected shearing force and to detect whether or not a thin-film object having a maximum friction coefficient different from a maximum stationary friction coefficient between the fingertips is grasped between the fingertips on the basis of the calculation result.

Accordingly, the above-described embodiments of the present invention allow for the capability to accurately detect that a thin-film object is in a grasped state in a robot hand device.

BRIEF DESCRIPTION OF THE DRAWINGS

FIG. 12 is a flow chart illustrating an object grasp determination process a;

DESCRIPTION OF THE PREFERRED EMBODIMENTS

First, a grasp detection technique according to an embodiment of the present invention will be described with reference to FIGS. 1 to 4.

FIGS. 1 to 4 illustrate an example of the external configuration of fingers equipped in a robot hand device.

Figure 1:
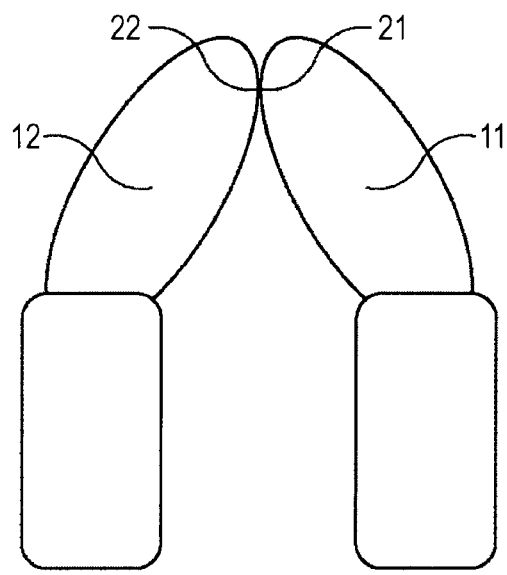
FIG. 1 illustrates an example of fingertips equipped in a robot hand device according to an embodiment of the present invention.

FIG. 1 illustrates a state where fingertips of two fingers are in contact with each other.

The fingers in the robot hand device according to this embodiment include fingertips 11 and 12. The fingertips 11 and 12 may be composed of, for example, silicon rubber.

In the state shown in FIG. 1, the fingertips 11 and 12 are in contact with each other at a contact point 21 of the fingertip 11 and a contact point 22 of the fingertip 12.

In the state shown in FIG. 1, the robot hand device applies a force $f_N$ in the normal direction (referred to as "normal force $f_N$" hereinafter) of the contact between the contact point 21 of the fingertip 11 and the contact point 22 of the fingertip 12. Moreover, in this state, the robot hand device also applies a force $f_T$ in the shearing direction of the contact ("referred to as "shearing force $f_T$" hereinafter) to the fingertips 11 and 12. The robot hand device measures the positional relationship between the fingertips 11 and 12 in this state so as to confirm whether the fingertips 11 and 12 have slid.

A friction coefficient μ of the fingertip 11 or 12 with respect to another object (in the example of FIG. 1, the other fingertip 12 or 11) can be determined from the following equation (1):

$$\mu = f_T/f_N \quad (1)$$

A maximum stationary friction coefficient $\mu_{T0}$ between the fingertips 11 and 12 is a friction coefficient μ just before the fingertips 11 and 12 begin to slide. Thus, the robot hand device measures the friction coefficient μ while applying a shearing force $f_T$ sufficient for sliding the fingertips 11 and 12 so that the measurement value obtained just before the fingertips 11 and 12 begin sliding can be acquired as a maximum stationary friction coefficient $\mu_{T0}$. Alternatively, the robot hand device may perform such measurement for a certain time period so that the maximum measurement value within that certain time period can be acquired as a maximum stationary friction coefficient $\mu_{T0}$.

In this manner, the maximum stationary friction coefficient $\mu_{T0}$ between the fingertips 11 and 12 can be determined.

A maximum stationary friction coefficient is a value that varies depending on the material of a contacting object. For example, when a thin-film object is grasped by the fingertips 11 and 12, a maximum friction coefficient $\mu_{S0}$ between the fingertips 11 and 12 and the thin-film object (simply referred to as "maximum friction coefficient $\mu_{S0}$ of thin-film object" hereinafter) should be different from the maximum stationary friction coefficient $\mu_{T0}$ between the fingertips 11 and 12. Therefore, a grasp of the thin-film object can be detected with high accuracy by utilizing the relationship between the maximum stationary friction coefficient $\mu_{T0}$ between the fingertips 11 and 12 and the maximum friction coefficient $\mu_{S0}$ of thin-film object. The maximum friction coefficient $\mu_{S0}$ of thin-film object will be described below with reference to FIGS. 2 to 4.

Figure 2:
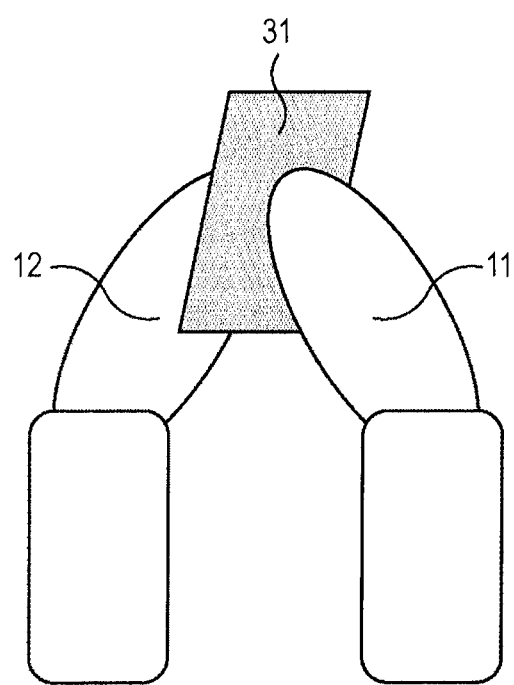
FIG. 2 is a perspective view illustrating the fingertips grasping a thin-film object.

FIG. 2 is a perspective view illustrating the fingertip 11 and the fingertip 12 of the robot hand device grasping a thin-film object 31.

Figure 3:
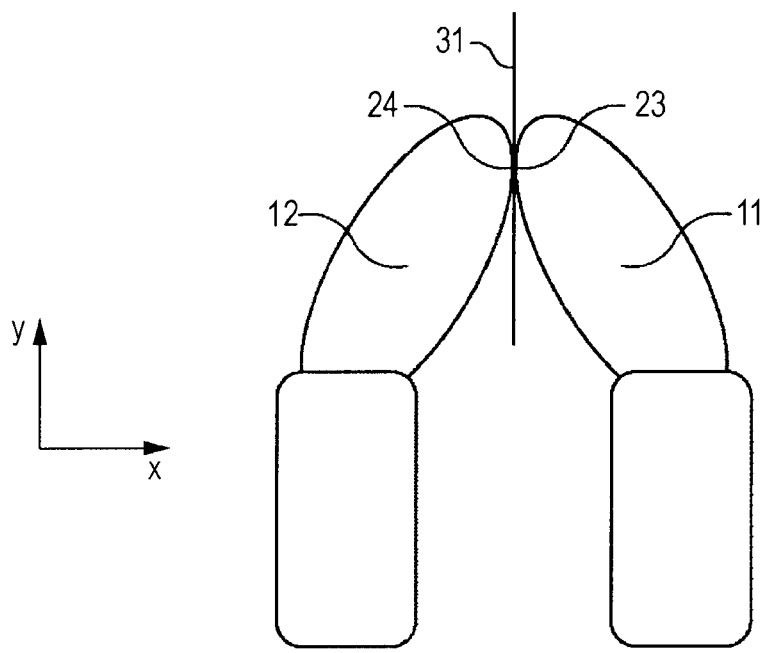
FIG. 3 is a side view illustrating the grasped state of the thin-film object by the fingertips shown in FIG. 2.

FIG. 3 is a side view illustrating the grasped state of the thin-film object 31 in FIG. 2. In FIG. 3, an x-axis direction indicates the normal direction of the fingertips 11 and 12, and a y-axis direction indicates the shearing direction. The x-axis direction and the y-axis direction similarly indicate their respective directions in other drawings.

The fingertip 11 is in contact with the thin-film object 31 at a contact point 23. The fingertip 12 is in contact with the thin-film object 31 at a contact point 24. Specifically, FIGS. 2 and 3 illustrate a state where the fingertips 11 and 12 are applying the normal force $f_N$ of a contact plane between the contact points 23 and 24 to the thin-film object 31.

Figure 4:
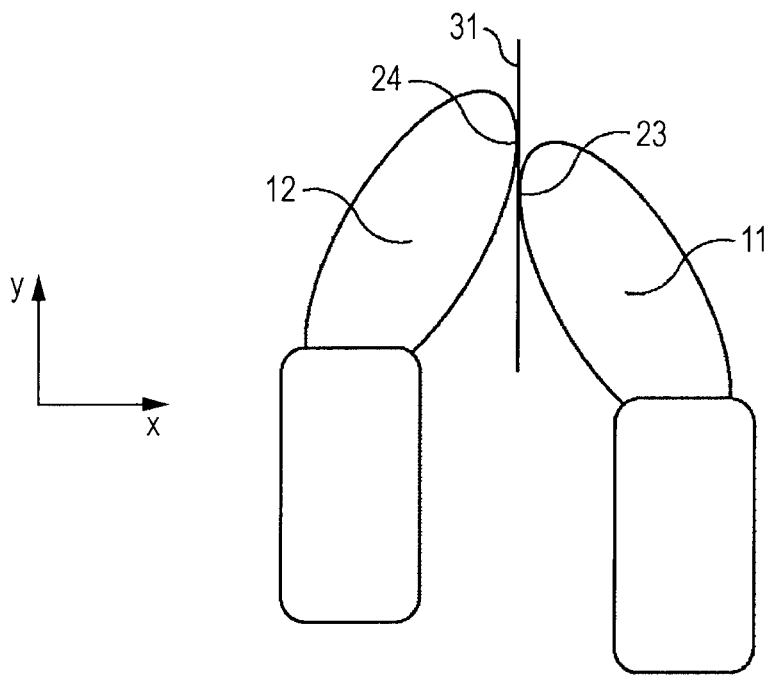
FIG. 4 illustrates a state where the fingertips are slid relative to the grasped thin-film object in FIG. 3.

FIG. 4 is a side view illustrating a state where the fingertip 12 is slid from the state shown in FIG. 3 while the thin-film object 31 is grasped by the fingertip 11 and the fingertip 12. The fingertip 11 is in contact with the thin-film object 31 at the contact point 23. The fingertip 12 is in contact with the thin-film object 31 at the contact point 24. Specifically, the state shown in FIG. 4 is such that, while the normal force $f_N$ of the contact plane of the thin-film object 31 with respect to the contact points 23 and 24 of the fingertips 11 and 12 is maintained, the fingertip 12 is slid as a result of applying the shearing force $f_T$ of the contact plane to the fingertip 12.

Assuming that, for example, the fingertips 11 and 12 are composed of silicon rubber and the thin-film object 31 is paper, the maximum stationary friction coefficient $\mu_{S0}$ of thin-film object and the maximum stationary friction coefficient $\mu_{T0}$ between the fingertips 11 and 12 in this case have a relationship expressed by the following equation (2):

$$\mu_{S0} < \mu_{T0} \quad (2)$$

For this reason, if a shearing force $f_T$ with a magnitude that still does not cause the fingertips 11 and 12 to start sliding against each other is applied thereto, the fingertip 12 may sometimes start to slide relatively against the thin-film object 31.

Consequently, for example, the robot hand device gradually increases the shearing force $f_T$ to a magnitude that still does not cause the fingertips 11 and 12 to start sliding against each other and continues to measure the friction coefficient $\mu$ in accordance with the equation (1) during that period so as to detect the maximum stationary friction coefficient $\mu_{S0}$ of thin-film object.

Here, the term "detect" has a broad concept that not only includes acquiring the value of maximum stationary friction coefficient $\mu_{S0}$ of thin-film object but also includes detecting that the friction coefficient $\mu$ has reached the maximum stationary friction coefficient $\mu_{S0}$ of thin-film object. The reason for this is that, as will be described below with reference to a flow chart shown in FIG. 6, it may not be necessary to acquire the actual value of the maximum stationary friction coefficient $\mu_{S0}$ of thin-film object to detect a thin-film object. Specifically, it is sufficient as long as the grasp of a thin-film object having a maximum friction coefficient $\mu_{S0}$ different from the maximum stationary friction coefficient $\mu_{T0}$ between the fingertips 11 and 12 can be detected, and therefore, it may not be necessary to determine the actual value of the maximum stationary friction coefficient $\mu_{S0}$ of thin-film object.

To summarize the above description, the grasp detection technique according to the embodiment of the present invention involves performing the following process. Specifically, the robot hand device, for example, changes the shearing force $f_T$ and measures the friction coefficient $\mu$ during that period in accordance with the equation (1). The robot hand device detects a grasp of a thin-film object having a maximum friction coefficient $\mu_{S0}$ different from a maximum stationary friction coefficient $\mu_{T0}$ between the fingertips 11 and 12 on the basis of this measurement result. Otherwise, the robot hand device detects that a thin-film object is not grasped by the fingertips 11 and 12 on the basis of this measurement result.

The grasp detection technique according to the embodiment of the present invention has been briefly described above with reference to FIGS. 1 to 4. A control device to which the grasp detection technique according to the embodiment of the present invention is applied, that is, a control device according to an embodiment of the present invention, will be described below with reference to FIG. 5 and onward.

Figure 5:
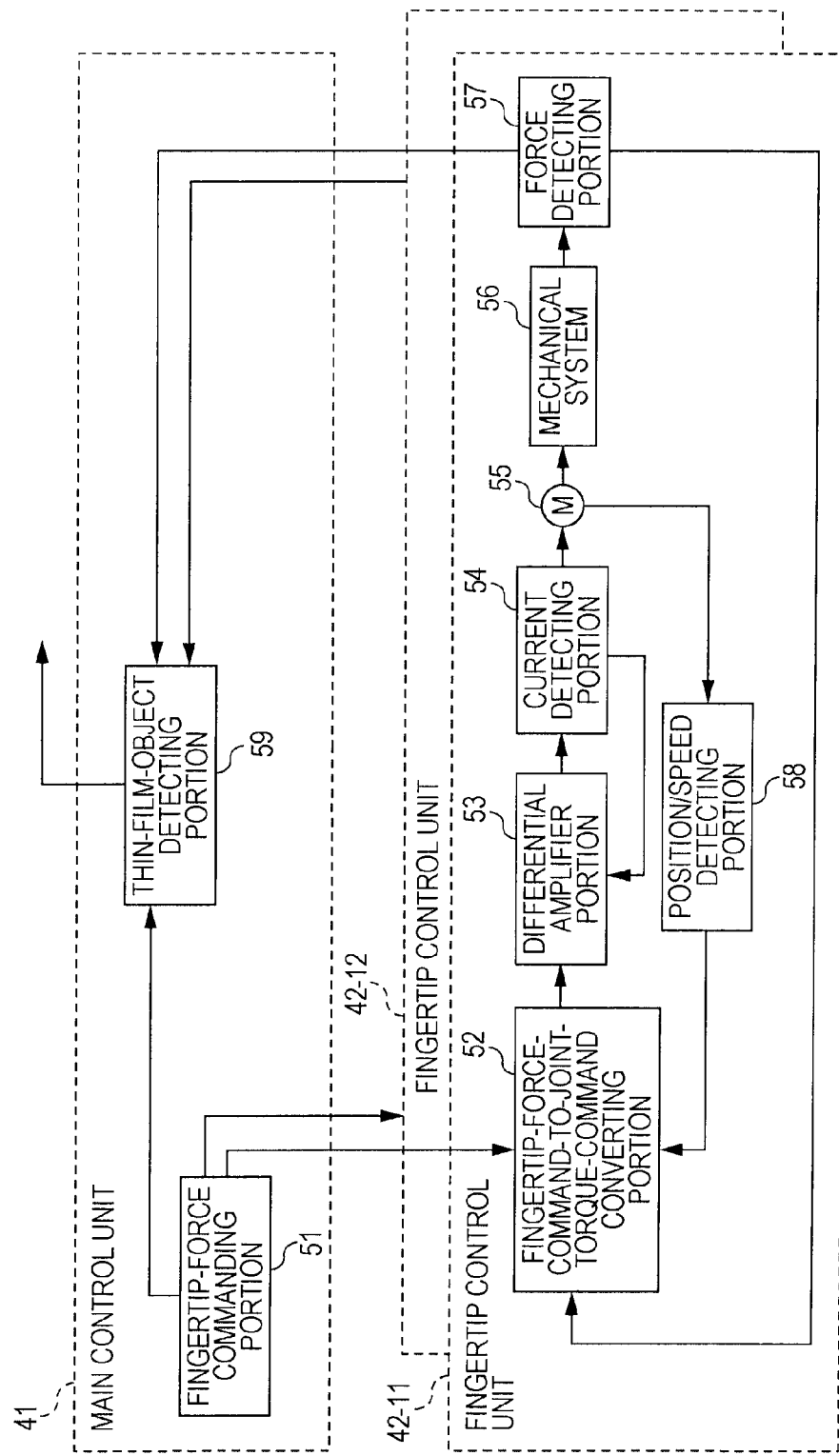
FIG. 5 is a block diagram of a force control system included in a robot hand device according to an embodiment of the present invention.

FIG. 5 is a functional block diagram illustrating a functional example of a part of the robot hand device, the part serving as a control device according to one embodiment of the present invention. Specifically, of the robot hand device, FIG. 5 only illustrates a main control unit 41 that is equivalent to a brain, a fingertip control unit 42-11 that controls the movement of only the fingertip 11, and a fingertip control unit 42-12 that controls the movement of only the fingertip 12. A force control system based on torque control by current feedback is used as a control system for the fingertip control units 42-11 and 42-12.

For simplifying the description, the description below will be focused on the fingertip control unit 42-11 for the fingertip 11. However, the description below similarly applies to the fingertip control unit 42-12 for the fingertip 12.

The main control unit 41 includes a fingertip-force commanding portion 51 and a thin-film-object detecting portion 59.

The fingertip control unit 42 includes a fingertip-force-command-to-joint-torque-command converting portion 52, a differential amplifier portion 53, a current detecting portion 54, a motor 55, a mechanical system 56, a force detecting portion 57, and a position/speed detecting portion 58.

The fingertip-force commanding portion 51 outputs a force command for the fingertip 11 (including a command value of the normal force $f_N$ and a command value of the shearing force $f_T$ of the fingertip 11 and referred to as "fingertip force command" hereinafter) to the fingertip control unit 42-11 and the thin-film-object detecting portion 59. A fingertip force command for the fingertip 12 is output to the fingertip control unit 42-12 and also to the thin-film-object detecting portion 59.

The fingertip-force-command-to-joint-torque-command converting portion 52 receives the fingertip force command for the fingertip 11 from the fingertip-force commanding portion 51. The fingertip-force-command-to-joint-torque-command converting portion 52 also receives feedback values from the force detecting portion 57, that is, forces detected by the force detecting portion 57 (a normal force $f_N$ and a shearing force $f_T$ of the fingertip 11). Moreover, the fingertip-force-command-to-joint-torque-command converting portion 52 receives feedback values from the position/speed detecting portion 58, that is, the position (such as the rotation angle) and the speed of the motor 55. Based on these feedback values, the fingertip-force-command-to-joint-torque-command converting portion 52 converts the fingertip force command to a joint torque command and outputs the joint torque command to the differential amplifier portion 53.

The differential amplifier portion 53 outputs a current command value to the current detecting portion 54 on the basis of the joint torque command and a current feedback value from the current detecting portion 54.

The current detecting portion 54 is configured to allow a current based on the current command value to flow through the motor 55 so as to detect the current. The detection result about the current is output to the differential amplifier portion 53 as a current feedback value.

The motor 55 rotates in response to the current and applies torque based on its rotation to the mechanical system 56.

With a mechanical output according to the torque applied from the motor 55, the mechanical system 56 causes the fingertip 11 to move. The operation of the mechanical system 56 generates a normal force $f_N$ and a shearing force $f_T$ on the fingertip 11.

The force detecting portion 57 detects the normal force $f_N$ and the shearing force $f_T$ of the fingertip 11 and outputs the detection results to the thin-film-object detecting portion 59 and the fingertip-force-command-to-joint-torque-command converting portion 52. Specifically, these detection results are output to the fingertip-force-command-to-joint-torque-command converting portion 52 as feedback values from the force detecting portion 57.

The position/speed detecting portion 58 detects the position (such as the rotation angle) and the speed of the motor 55 and outputs the detection results as feedback values to the fingertip-force-command-to-joint-torque-command converting portion 52.

The thin-film-object detecting portion 59 detects whether or not a thin-film object is grasped on the basis of the fingertip force command from the fingertip-force commanding portion 51 and at least one of the detection results about the forces from the fingertip control unit 42-11 and the fingertip control unit 42-12.

As one of processes to be performed by the robot hand device having the configuration shown in FIG. 5, a process of determining whether or not an object is grasped by the fingertips 11 and 12 (referred to as "object grasp determination process" hereinafter) will be described below.

Figure 6:
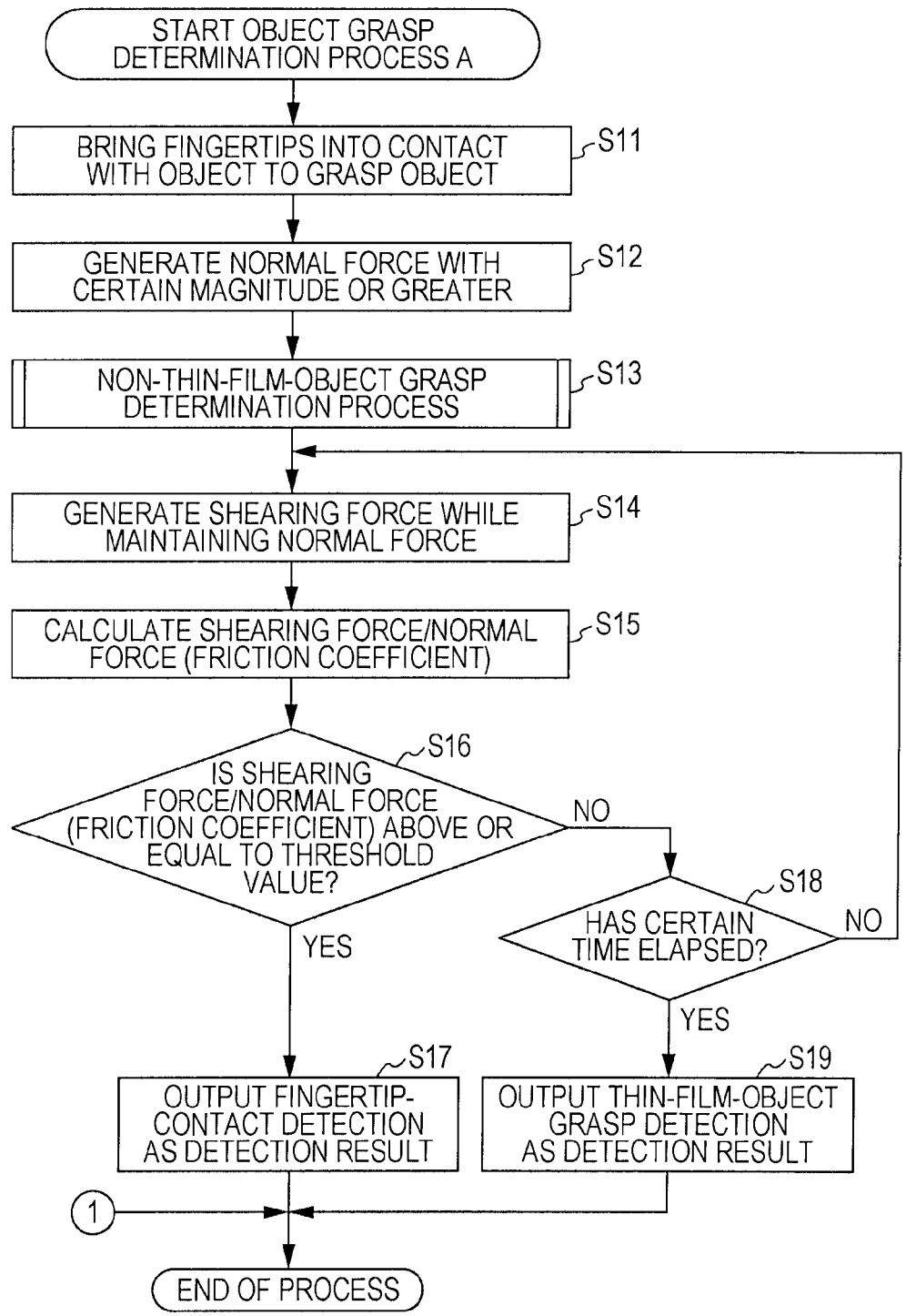
FIG. 6 is a flow chart illustrating an object grasp determination process A.

FIG. 6 is a flow chart illustrating an example of an object grasp determination process. To clearly differentiate this object grasp determination process from other examples of object grasp determination processes to be described later, the object grasp determination process of the example shown in FIG. 6 will specifically be referred to as "object grasp determination process A".

The object grasp determination process A in FIG. 6 is based on the precondition that the maximum stationary friction coefficient $\mu_{T0}$ of fingertips is already given. The maximum stationary friction coefficient $\mu_{T0}$ of fingertips can be preliminarily measured using the technique described with reference to FIG. 1. Based on the maximum stationary friction coefficient $\mu_{T0}$ of fingertips, it is assumed that a threshold value to be used in step S16 is preliminarily set. This threshold value will be described later.

When it is not necessary to differentiate between the fingertip control units 42-11 and 42-12, the term "fingertip control unit 42" will simply be used.

In step S11, the fingertip control unit 42 allows the fingertips 11 and 12 to come into contact with an object so as to cause them to grasp the object. Specifically, the fingertip-force commanding portion 51 outputs, to the fingertip control unit 42, for example, a fingertip force command that causes the fingertips 11 and 12 to close. Thus, the fingertip control unit 42 causes the fingertips 11 and 12 to come into contact with the object.

For example, when the thin-film object 31 shown in FIG. 2 is used as the object, the thin-film object 31 is set in the position shown in FIG. 2 as the result of step S11. In other words, the thin-film object 31 is given a certain positional orientation. However, due to an error or the like, it is difficult to confirm whether or not the thin-film object 31 is actually grasped by the fingertips 11 and 12 at the stage of step S11. For this reason, the process from step S12 and onward is performed.

In step S12, the fingertip control unit 42 causes the fingertips 11 and 12 to generate a normal force $f_N$ with a certain magnitude or greater.

In step S13, the thin-film-object detecting portion 59 determines whether or not the grasped object is an object that is thicker (referred to as "non-thin-film object" hereinafter) than a thin-film object. If it is determined that the grasped object is a non-thin-film object, the object grasp determination process A ends (after step S33 in a flow chart in FIG. 7 to be described later). In contrast, if it is determined that the grasped object is not a non-thin-film object, the process proceeds to step S14. A non-thin-film-object grasp determination process will be described in detail later with reference to the flow chart in FIG. 7.

In step S14, the fingertip control unit 42 causes the fingertips 11 and 12 to generate a shearing force $f_T$ while maintaining the normal force $f_N$.

The shearing force $f_T$ in this case may have a magnitude that causes the fingertips 11 and 12 to start sliding if a thin-film object is grasped between the fingertips 11 and 12 or may have a magnitude that does not cause the fingertips 11 and 12 to start sliding if the fingertips 11 and 12 are in contact with each other.

The results obtained after step S14, that is, the normal force $f_N$ and the shearing force $f_T$, are detected by the force detecting portion 57 and are supplied to the thin-film-object detecting portion 59. The process then proceeds to step S15.

In step S15, the thin-film-object detecting portion 59 performs a calculation by dividing the shearing force $f_T$ by the normal force $f_N$, thereby acquiring a friction coefficient $\mu$. In other words, in step S15, the calculation is performed using the aforementioned equation (1).

In step S16, the thin-film-object detecting portion 59 determines whether or not the calculated value of $f_T/f_N$ (friction coefficient $\mu$) is above or equal to a threshold value.

As mentioned above, a threshold value is a friction coefficient determined on the basis of the maximum stationary friction coefficient $\mu_{T0}$ of fingertips.

In detail, considering the relationship in the equation (2), for example, a friction coefficient $\mu_{TH}$ based on the following equation (3) can be used as the threshold value.

$$\mu_{S0} < \mu_{TH} < \mu_{T0} \qquad (3)$$

If the value of $f_T/f_N$ (friction coefficient $\mu$) is above or equal to the threshold value, it is determined to be YES in step S16, and the process proceeds to step S17.

In step S17, the thin-film-object detecting portion 59 outputs fingertip-contact detection as a detection result.

The term "fingertip-contact detection" means that the state shown in FIG. 1, that is, a state where an object (a thin-film object or a non-thin-film object) is not grasped between the fingertips 11 and 12 and the fingertips 11 and 12 are in contact with each other, is detected.

In contrast, if the value of $f_T/f_N$ (friction coefficient $\mu$) is below the threshold value, it is determined to be NO in step S16, and the process proceeds to step S18.

In step S18, the thin-film-object detecting portion 59 determines whether or not a certain time has elapsed.

If the certain time has not elapsed, it is determined to be NO in step S18, and the process returns to step S14 and the steps thereafter are repeated. Specifically, the friction coefficient $\mu$ is re-measured in steps S14 and S15, and the re-measured result and the threshold value are re-compared in step S16. The reason the friction coefficient $\mu$ is re-measured until the elapse of certain time in this manner is that it is difficult to detect the maximum friction coefficient on the basis of a single measurement result of a friction coefficient $\mu$.

If the certain time elapses and the value of $f_T/f_N$ (friction coefficient $\mu$) remains to be smaller than the threshold value regardless of repeated measurements of the friction coefficient $\mu$ in this manner, it is determined to be YES in step S18, and the process proceeds to step S19.

In step S19, the thin-film-object detecting portion 59 outputs thin-film-object grasp detection as a detection result.

The term "thin-film-object grasp detection" means that the state shown in FIGS. 2 to 4, that is, a state where a thin-film object, such as the thin-film object 31, is grasped between the fingertips 11 and 12 and the fingertips 11 and 12 are slid against the thin-film object, is detected. In other words, the term "thin-film-object grasp detection" means that a maximum stationary friction coefficient $\mu_{S0}$ of thin-film object is detected.

Figure 7:
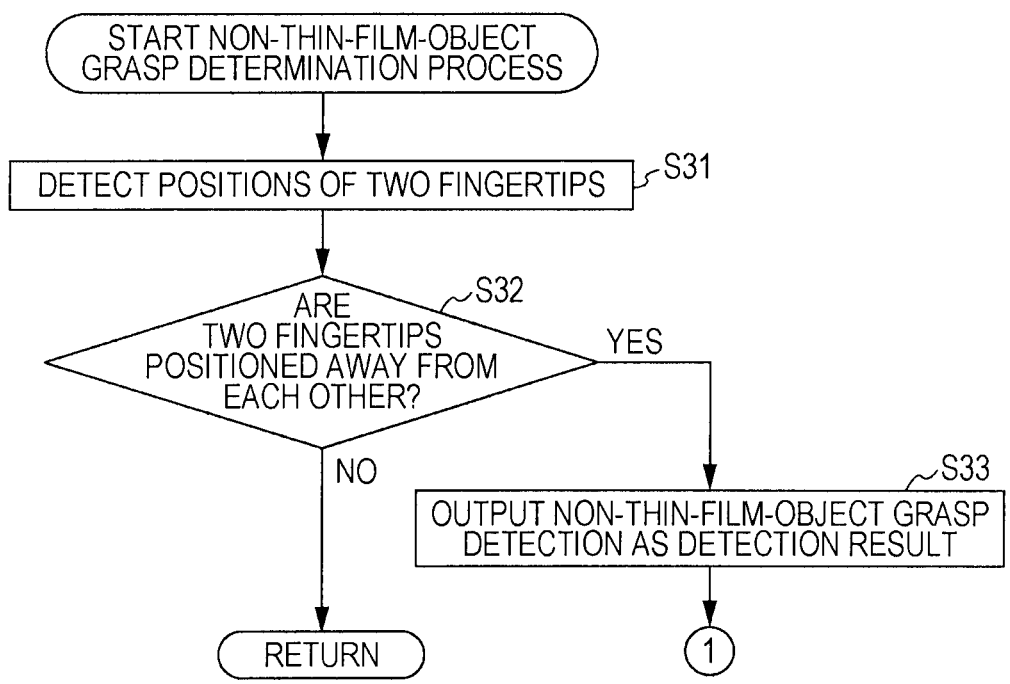
FIG. 7 is a flow chart illustrating a non-thin-film-object grasp determination process shown in FIG. 6.

The non-thin-film-object grasp determination process in step S13 will now be described with reference to FIG. 7.

In step S31, the thin-film-object detecting portion 59 detects the positions of the two fingertips 11 and 12. For example, although an arrow is not shown in FIG. 5, it is assumed that the detection results of the position/speed detecting portion 58 are supplied to the thin-film-object detecting portion 59 from the fingertip control unit 42-11 for the fingertip 11 and the fingertip control unit 42-12 for the fingertip 12. Based on these detection results, the position/speed detecting portion 58 detects the positions of the fingertips 11 and 12.

In step S32, the thin-film-object detecting portion 59 determines whether or not the two fingertips 11 and 12 are positioned away from each other.

If the two fingertips 11 and 12 are not positioned away from each other, it is determined to be NO in step S32. In other words, it is determined that a non-thin-film object is not grasped between the fingertips 11 and 12. Thus, the process proceeds to step S14 in FIG. 6.

In contrast, if the two fingertips 11 and 12 are positioned away from each other, it is determined to be YES in step S32. In other words, it is determined that a non-thin-film object is grasped between the fingertips 11 and 12. Thus, the process proceeds to step S33.

In step S33, the thin-film-object detecting portion 59 outputs non-thin-film-object grasp detection as a detection result.

The term "non-thin-film-object grasp detection" means that a state where a non-thin-film object is grasped between the fingertips 11 and 12 is detected.

Figure 8:
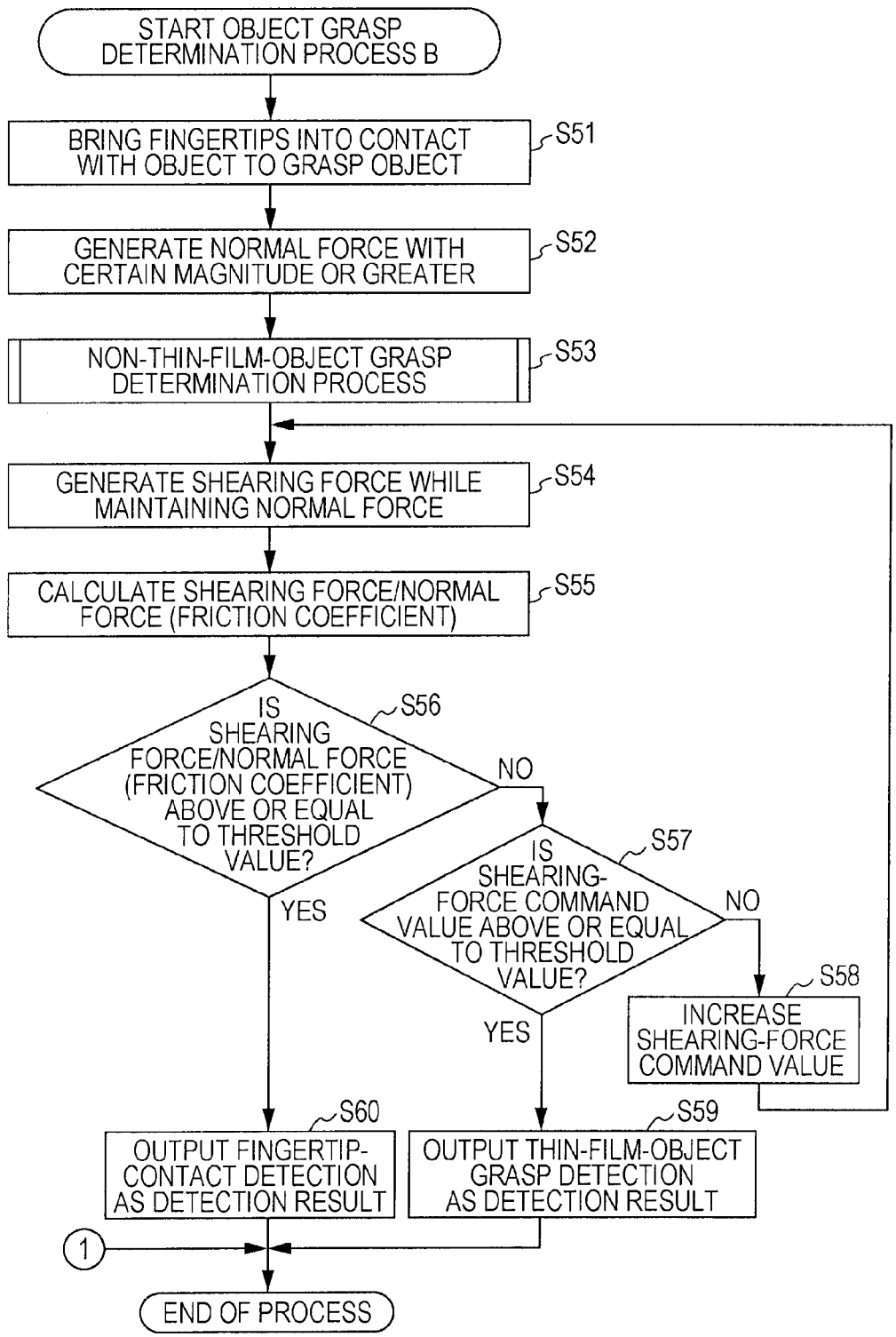
FIG. 8 is a flow chart illustrating an object grasp determination process B.

FIG. 8 is a flow chart illustrating another example of an object grasp determination process, which is different from the example shown in FIG. 6. To clearly differentiate this object grasp determination process from other examples of object grasp determination processes, such as the object grasp determination process A shown in FIG. 6, the object grasp determination process of the example shown in FIG. 8 will specifically be referred to as "object grasp determination process B".

Similar to the object grasp determination process A in FIG. 6, the object grasp determination process B in FIG. 8 is based on the precondition that the maximum stationary friction coefficient $\mu_{T0}$ of fingertips is already given. The maximum stationary friction coefficient $\mu_{T0}$ of fingertips can be preliminarily measured using the technique described with reference to FIG. 1. Based on the maximum stationary friction coefficient $\mu_{T0}$ of fingertips, it is assumed that a threshold value to be used in step S56 is preliminarily set.

Steps S51 to S55 in FIG. 8 are basically the same as steps S11 to S15 in FIG. 6. Therefore, step S56 and onward will be described below.

In step S56, the thin-film-object detecting portion 59 determines whether or not the calculated value of $f_T/f_N$ (friction coefficient $\mu$) is above or equal to a threshold value.

As mentioned above, a threshold value is a friction coefficient determined on the basis of the maximum stationary friction coefficient $\mu_{T0}$ of fingertips. Specifically, for example, the friction coefficient $\mu_{TH}$ in the aforementioned equation (3) can be used as the threshold value.

If the value of $f_T/f_N$ (friction coefficient $\mu$) is above or equal to the threshold value, it is determined to be YES in step S56, and the process proceeds to step S60.

In step S60, the thin-film-object detecting portion 59 outputs fingertip-contact detection as a detection result.

In contrast, if the value of $f_T/f_N$ (friction coefficient $\mu$) is below the threshold value, it is determined to be NO in step S56, and the process proceeds to step S57.

In step S57, the thin-film-object detecting portion 59 determines whether or not a command value of the shearing force $f_T$ is above or equal to a threshold value.

The command value of the shearing force $f_T$ in this case will be referred to as "shearing-force command value $f_{TCMD}$" hereinafter.

The threshold value used in step S57 will be referred to as "shearing-force threshold value $f_{TTH}$". The shearing-force threshold value $f_{TTH}$ is set as in the following equation (4). In the equation (4), $f_{NCMD}$ denotes a command value for generating the normal force $f_N$ in step S52 (referred to as "normal-force command value $f_{NCMD}$" hereinafter).

$$\mu_{TH} \times F_{NCMD} < F_{TTH} < \mu_{T0} \times f_{NCMD} \qquad (4)$$

If the shearing-force command value $f_{TCMD}$ is below the shearing-force threshold value $f_{TTH}$, it is determined to be NO in step S57, and the process proceeds to step S58. In step S58, the fingertip-force commanding portion 51 increases the shearing-force command value $f_{TCMD}$. Subsequently, the process returns to step S54 and the steps thereafter are repeated. Specifically, the friction coefficient $\mu$ is re-measured in steps S54 and S55 every time the shearing-force command value $f_{TCMP}$ is increased, and the re-measured result and the threshold value are re-compared in step S56.

Figure 9:
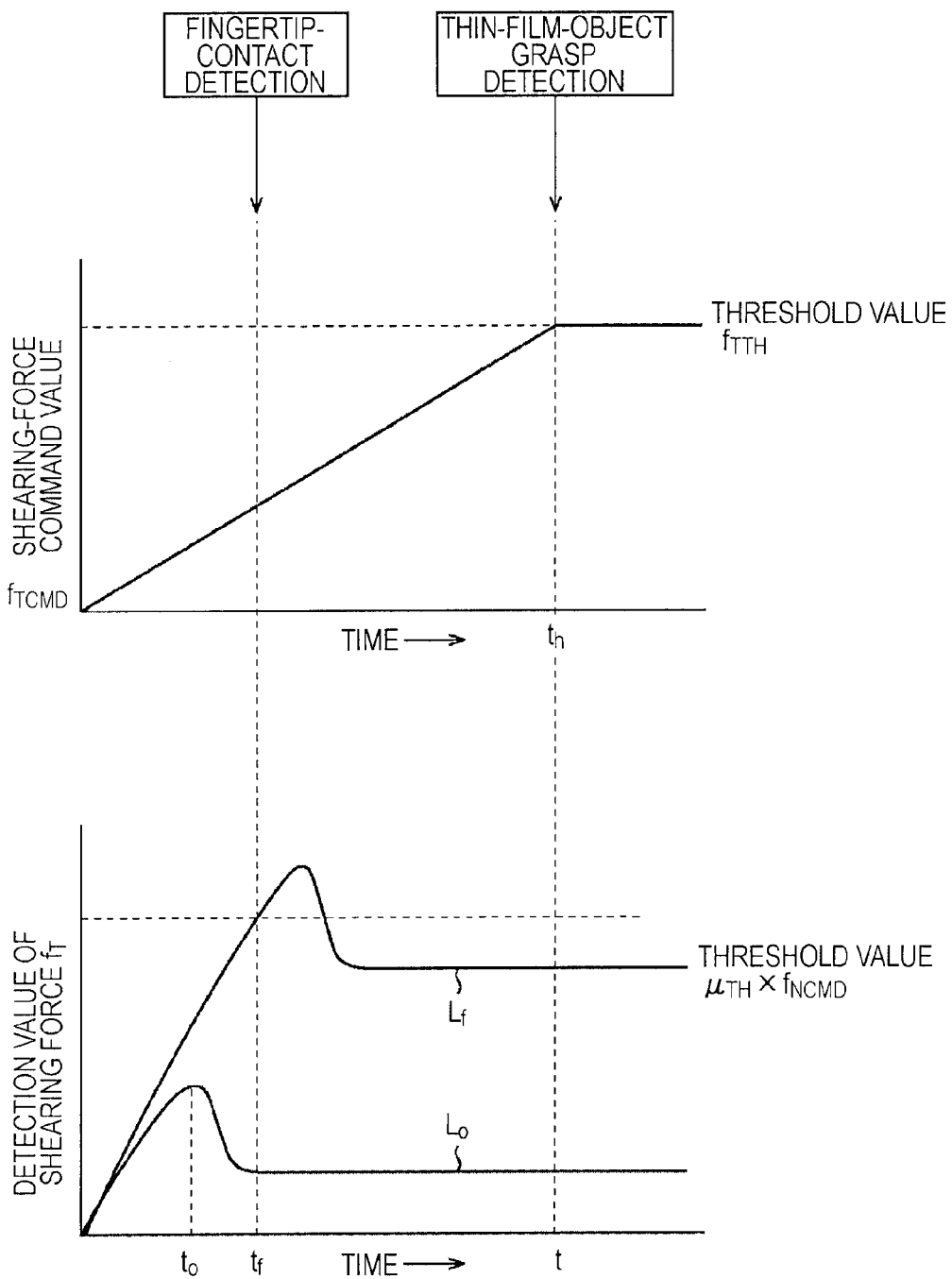
FIG. 9 is a diagram for explaining the object grasp determination process B shown in FIG. 8.

In other words, as shown in the upper half of FIG. 9, the shearing-force command value $f_{TCMD}$ increases in the form of a ramp as time elapses.

Specifically, the normal force $f_N$ maintains its magnitude produced in step S52. Thus, as is apparent from the equation (1), the magnitude of $f_T/f_N$ (friction coefficient $\mu$) calculated in step S55 is proportional to the magnitude of the shearing force $f_T$. The lower half of FIG. 9 illustrates the time transition of a detection value of the shearing force $f_T$, among the detection values of the force detecting portion 57, as a parameter for showing the time transition of the value of $f_T/f_N$ (friction coefficient $\mu$) calculated in step S55.

For example, it is assumed that the fingertips 11 and 12 are in the state shown in FIG. 1, that is, in a state where an object (a thin-film object or a non-thin-film object) is not grasped therebetween and the fingertips 11 and 12 are in contact with each other.

In this case, when the loop from step S54 to step S58 is repeated, the shearing-force command value $f_{TCMD}$ increases in the form of a ramp as time elapses, as shown in the upper half of FIG. 9. Accordingly, the detection value of the shearing force $f_T$ similarly increases along a curve line $L_f$, as shown in the lower half of FIG. 9.

Specifically, until time $t_f$, the detection value of the shearing force $f_T$ does not exceed a value of $\mu_{TH}$ (threshold value)× $f_{NCMD}$ (normal-force command value). Thus, it is constantly determined to be NO in step S56. Furthermore, as is apparent from the upper half of FIG. 9, the shearing-force command value $f_{TCMD}$ is constantly below the threshold value $f_{TTH}$ so that it is determined to be NO in step S57. Thus, the loop from step S54 to step S58 is repeated.

Upon reaching time $t_f$, the detection value of the shearing force $f_T$ becomes equal to the value of $\mu_{TH}$ (threshold value)× $f_{NCMD}$ (normal-force command value). In consequence, it is subsequently determined to be YES in step S56, and fingertip-contact detection is output in step S60.

In contrast, it is assumed that the fingertips 11 and 12 are in the state shown in FIGS. 2 and 3, that is, in a state where a thin-film object such as the thin-film object 31 is grasped therebetween.

In this case, when the loop from step S54 to step S58 is repeated, the shearing-force command value $f_{TCMD}$ increases in the form of a ramp as time elapses, as shown in the upper half of FIG. 9. Accordingly, the detection value of the shearing force $f_T$ similarly increases along a curve line $L_0$, as shown in the lower half of FIG. 9.

However, when reaching time $t_0$, the fingertips 11 and 12 are in the state shown in FIG. 4, that is, in a state where they are slid against a thin-film object. The friction coefficient $\mu$ at time $t_0$ is the maximum stationary friction coefficient $\mu_{S0}$ of thin-film object. In other words, the detection value of the shearing force $f_T$ reaches its maximum at time $t_0$. Subsequently, since the friction coefficient $\mu$ becomes a kinetic friction coefficient, the friction coefficient $\mu$ becomes lower than the maximum stationary friction coefficient $\mu_{S0}$ of thin-film object. Accordingly, as shown with the curve line $L_0$ in the lower half of FIG. 9, the detection value of the shearing force $f_T$ reaches its maximum at time $t_0$ and maintains a value lower than the maximum value thereafter.

Therefore, the detection value of the shearing force $f_T$ does not exceed the value of $\mu_{TH}$ (threshold value)× $F_{NCMD}$ (normal-force command value). In other words, it is constantly and continuously determined to be NO in step S56. Specifically, when the loop from step S54 to step S58 is repeated until time $t_h$, the shearing-force command value $f_{TCMD}$ increases in the form of a ramp as time elapses, as shown in the upper half of FIG. 9.

Upon reaching time $t_h$, it is determined to be YES in step S57, and the process proceeds to step S59 in FIG. 8. In step S59, the thin-film-object detecting portion 59 outputs thin-film-object grasp detection as a detection result.

Figure 10:
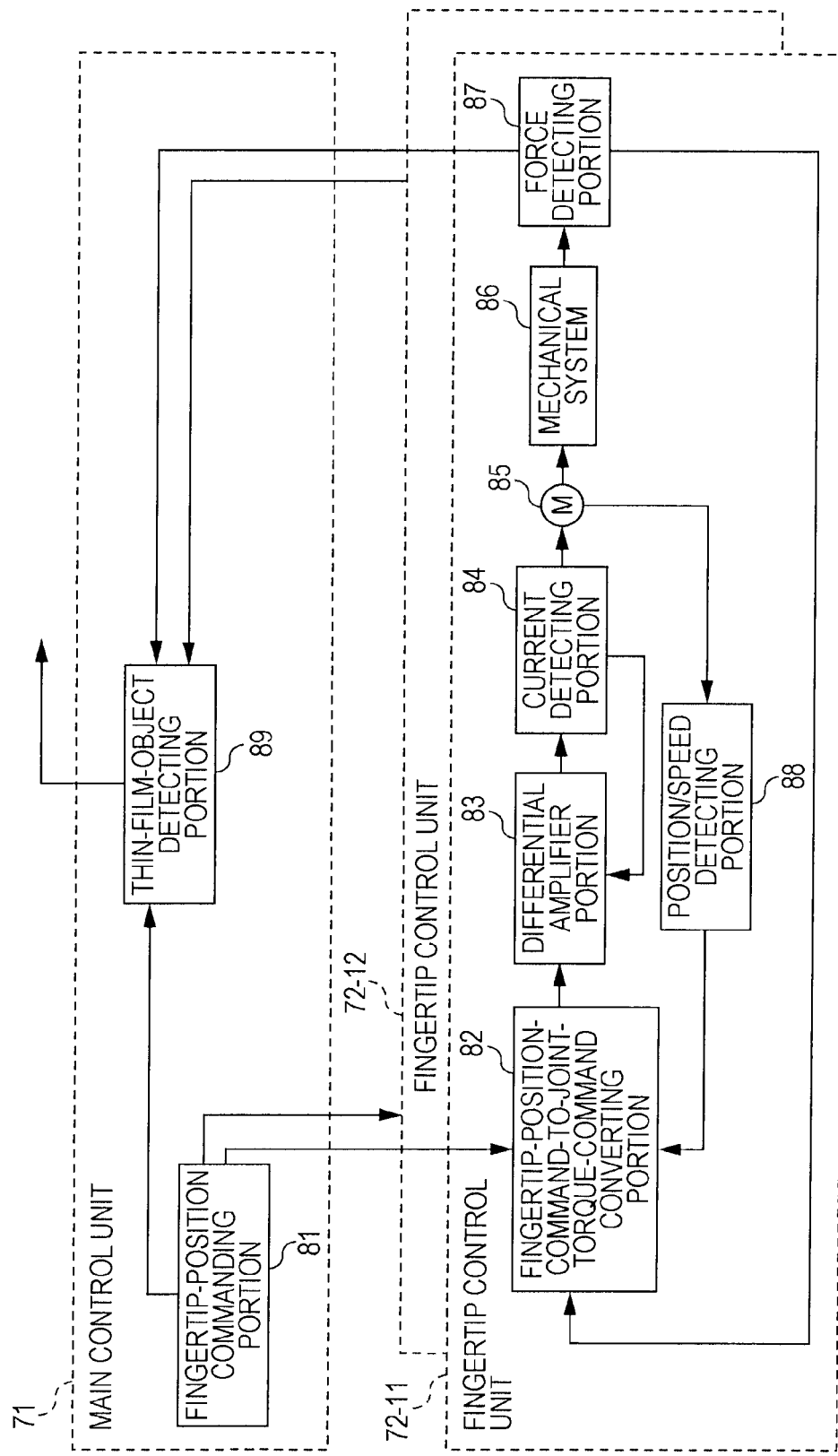
FIG. 10 is a block diagram illustrating a position control system included in a robot hand device according to an embodiment of the present invention.

FIG. 10 is a functional block diagram illustrating a functional example, different from that in FIG. 5, of a part of the robot hand device, the part serving as a control device according to another embodiment of the present invention. Specifically, of the robot hand device, FIG. 10 only illustrates a main control unit 71 that is equivalent to a brain, a fingertip control unit 72-11 that controls the movement of only the fingertip 11, and a fingertip control unit 72-12 that controls the movement of only the fingertip 12. A position control system based on torque control by current feedback is used as a control system for the fingertip control units 72-11 and 72-12.

Specifically, in contrast to the force control system being used in the configuration example in FIG. 5, a position control system is used in the configuration example in FIG. 10. Therefore, in the example in FIG. 10, there is no feedback from the fingertip control unit 72-11 and a force detecting portion 87.

Furthermore, since a command to be sent by a commanding portion relates to a position, a fingertip-position commanding portion 81 is used in the example in FIG. 10 in contrast to the fingertip-force commanding portion 51 being used in the example in FIG. 5. Moreover, in contrast to the fingertip-force-command-to-joint-torque-command converting portion 52 being used in each of the fingertip control units 42-11 and 42-12 in the example in FIG. 5, a fingertip-position-command-to-joint-torque-command converting portion 82 is used in each of the fingertip control units 72-11 and 72-12 in the example in FIG. 10.

The remaining configuration in the example in FIG. 10 is basically the same as that in the example in FIG. 5. In other words, a differential amplifier portion 83 to a thin-film-object detecting portion 89 are basically the same as the differential amplifier portion 53 to the thin-film-object detecting portion 59, respectively. Therefore, the descriptions of these components will not be repeated.

Figure 11:
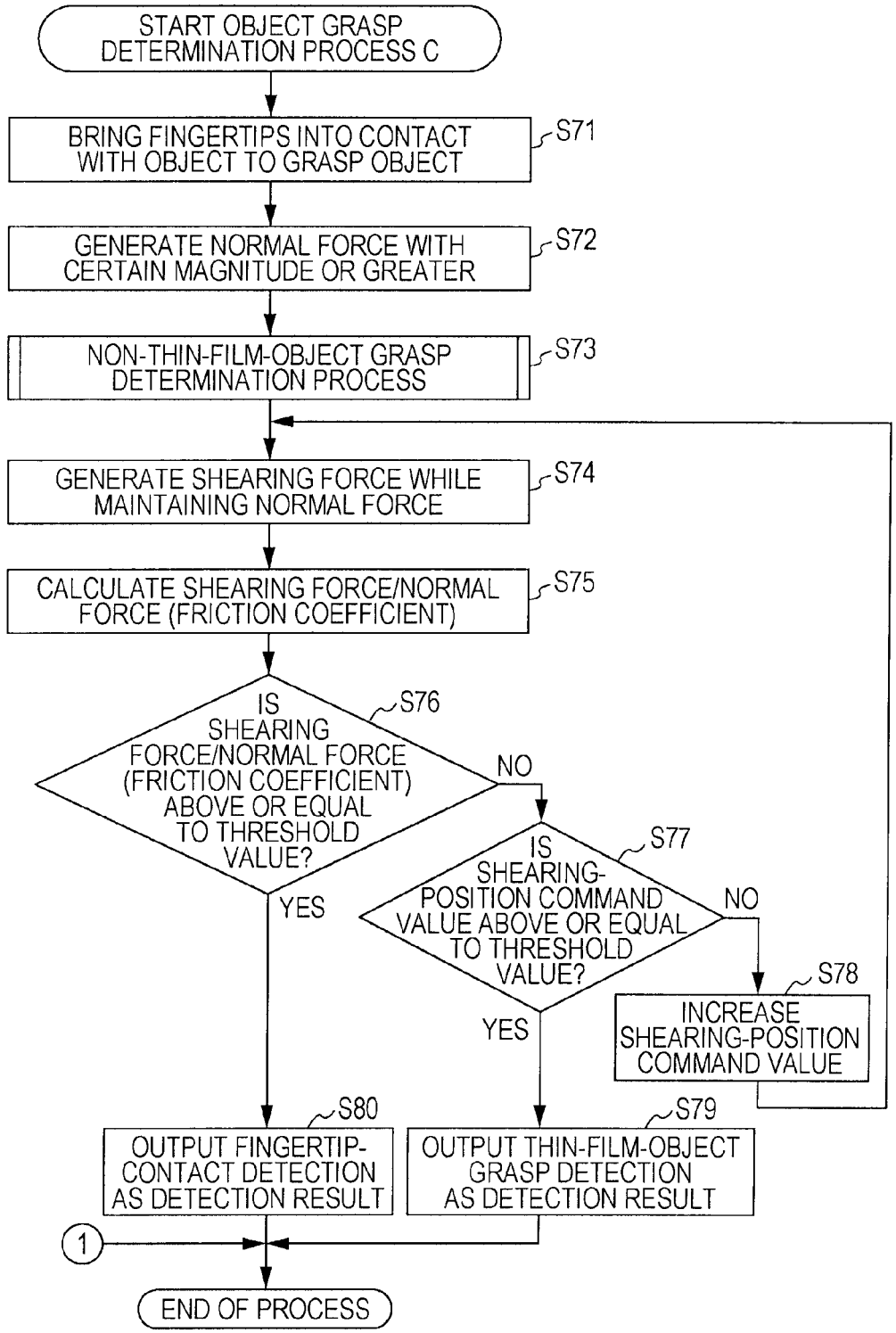
FIG. 11 is a flow chart illustrating an object grasp determination process C.

FIG. 11 is a flow chart illustrating another example of an object grasp determination process, which is different from the example shown in FIG. 8, performed in the robot hand device having the configuration shown in FIG. 10. To clearly differentiate this object grasp determination process from other examples of object grasp determination processes, such as the object grasp determination process B shown in FIG. 8, the object grasp determination process of the example shown in FIG. 11 will specifically be referred to as "object grasp determination process C".

Similar to the object grasp determination process B in FIG. 8, the object grasp determination process C in FIG. 11 is based on the precondition that the maximum stationary friction coefficient $\mu_{T0}$ of fingertips is already given. The maximum stationary friction coefficient $\mu_{T0}$ of fingertips can be preliminarily measured using the technique described with reference to FIG. 1. Based on the maximum stationary friction coefficient $\mu_{T0}$ of fingertips, it is assumed that a threshold value to be used in step S76 is preliminarily set.

When it is not necessary to differentiate between the fingertip control units 72-11 and 72-12, the term "fingertip control unit 72" will simply be used.

In step S71, the fingertip control unit 72 allows the fingertips 11 and 12 to come into contact with an object so as to cause them to grasp the object. Specifically, the fingertip-position commanding portion 81 outputs, to the fingertip control unit 72, for example, a fingertip position command that causes the fingertips 11 and 12 to close. Thus, the fingertip control unit 72 causes the fingertips 11 and 12 to come into contact with the object.

In step S72, the fingertip control unit 72 causes the fingertips 11 and 12 to generate a normal force $f_N$ with a certain magnitude or greater.

For example, the fingertips 11 and 12 are composed of silicon rubber, and the spring constant of the silicon rubber in the normal direction is denoted by $K_N$. The distance between the fingertips 11 and 12 in the x-axis direction (normal direction) shown in FIG. 4 is denoted by $\Delta x$ (simply referred to as "distance $\Delta x$ between the fingertips in the x-axis direction" hereinafter). In this case, the normal force $f_N$ and the distance $\Delta x$ between the fingertips in the x-axis direction have a relationship expressed by the following equations (5) and (6):

$$f_N = K_N \cdot \Delta x \tag{5}$$

$$\Delta x = f_N / K_N \tag{6}$$

It is assumed that the fingertip-position commanding portion 81 outputs, to the fingertip control unit 72, a fingertip position command that causes the fingertips 11 and 12 to come into contact with each other by moving only the fingertip 12 but not the fingertip 11. If a position command value of the fingertip 12 in the x-axis direction is denoted by $x_{12CMD}$ (simply referred to as "normal-position command value $x_{12CMD}$" hereinafter) and a position command value in the x-axis direction at the contact position of the fingertips 11 and 12 is denoted by $x_{12CMDC}$, a relationship expressed by the following equation (7) is satisfied:

$$x_{12CMD} = x_{12CMDC} + f_N / K_N \tag{7}$$

In step S73, the thin-film-object detecting portion 89 performs the non-thin-film-object grasp determination process described above with reference to FIG. 7. If it is determined that the grasped object is a non-thin-film object, the object grasp determination process C ends (after step S33 in the flow chart in FIG. 7 described above). In contrast, if it is determined that the grasped object is not a non-thin-film object, the process proceeds to step S74.

In step S74, the fingertip control unit 72 causes the fingertips 11 and 12 to generate a shearing force $f_T$ while maintaining the normal force $f_N$.

For example, the fingertips 11 and 12 are composed of silicon rubber, and the spring constant of the silicon rubber in the shearing direction is denoted by $K_T$. The distance between the fingertips 11 and 12 in the y-axis direction (shearing direction) shown in FIG. 4 is denoted by $\Delta y$ (simply referred to as "distance $\Delta y$ between the fingertips in the y-axis direction" hereinafter). In this case, the shearing force $f_T$ and the distance $\Delta y$ between the fingertips in the y-axis direction have a relationship expressed by the following equations (8) and (9):

$$f_T = K_T \cdot \Delta y \tag{8}$$

$$\Delta y = f_T / K_T \tag{9}$$

It is assumed that the fingertip-position commanding portion 81 outputs, to the fingertip control unit 72, a fingertip position command that causes the fingertips 11 and 12 to come into contact with each other by moving only the fingertip 12 but not the fingertip 11. If a position command value of the fingertip 12 in the y-axis direction is denoted by $y_{12CMD}$ (simply referred to as "shearing-position command value $y_{12CMD}$" hereinafter) and a position command value in the y-axis direction at the contact position of the fingertips 11 and 12 is denoted by $y_{12CMDC}$, a relationship expressed by the following equation (10) is satisfied:

$$y_{12CMD} = y_{12CMDC} + f_T/K_T \quad (10)$$

The fingertip-position commanding portion 81 outputs the normal-position command value $x_{12CMD}$ for the fingertip 12 and the shearing-position command value $y_{12CMD}$ for the fingertip 12 respectively expressed by the equations (7) and (10) as position command values for the fingertip 12.

The results obtained from step S74, that is, the normal force $f_N$ and the shearing force $f_T$, are detected by the force detecting portion 87 and are supplied to the thin-film-object detecting portion 89. The process then proceeds to step S75.

In step S75, the thin-film-object detecting portion 89 performs a calculation by dividing the shearing force $f_T$ by the normal force $f_N$, thereby acquiring a friction coefficient $\mu$. In other words, in step S75, the calculation is performed using the aforementioned equation (1).

In step S76, the thin-film-object detecting portion 89 determines whether or not the calculated value of $f_T/f_N$ (friction coefficient $\mu$) is above or equal to a threshold value.

As mentioned above, a threshold value is a friction coefficient determined on the basis of the maximum stationary friction coefficient $\mu_{T0}$ of fingertips. Specifically, for example, the threshold value $\mu_{TH}$ in the aforementioned expression (3) can be used as the threshold value.

If the value of $f_T/f_N$ (friction coefficient $\mu$) is above or equal to the threshold value, it is determined to be YES in step S76, and the process proceeds to step S80 where fingertip-contact detection is output as a detection result.

In contrast, if the value of $f_T/f_N$ (friction coefficient $\mu$) is below the threshold value, it is determined to be NO in step S76, and the process proceeds to step S77.

In step S77, the thin-film-object detecting portion 89 determines whether or not the shearing-position command value $y_{12CMD}$ is above or equal to a threshold value.

The threshold value used in step S77 will be referred to as "shearing-position threshold value $y_{12TTH}$". The shearing-position threshold value $y_{12TTH}$ is set in accordance with the following equation (11):

$$y_{12CMDC} + \mu_{TH} \times f_N/K_T < y_{12TTH} < y_{12CMDC} + \mu_{T0} \times f_N/K_T \quad (11)$$

If the shearing-position command value $y_{12CMD}$ is below the shearing-position threshold value $y_{12TTH}$, it is determined to be NO in step S77, and the process proceeds to step S78. In step S78, the fingertip-position commanding portion 81 increases the shearing-position command value $y_{12CMD}$. Subsequently, the process returns to step S74 and the steps thereafter are repeated. Specifically, the friction coefficient $\mu$ is re-measured in steps S74 and S75 every time the shearing-position command value $y_{12CMD}$ is increased, and the re-measured result and the threshold value are re-compared in step S76.

When it is determined to be YES in step S77, the process proceeds to step S79. In step S79, the thin-film-object detecting portion 89 outputs thin-film-object grasp detection as a detection result.

Specifically, it is readily apparent from comparing the flow charts shown in FIGS. 8 and 11 that, in contrast to the example in FIG. 8 in which the subject to be compared with the threshold value in step S57 is a shearing-force command value, the subject to be compared with the threshold value in step S77 is a shearing-position command value in the example in FIG. 11. Moreover, in contrast to the shearing-force command value being increased in step S58 in the example of FIG. 8, the shearing-position command value is increased in step S78 in the example of FIG. 11. The remaining steps are basically the same between FIGS. 8 and 11. This implies that whether the robot hand device has the configuration shown in FIG. 5 or FIG. 10, the object grasp determination process can basically be performed in a similar manner.

The above description is directed to a case where the friction coefficient between the fingertips 11 and 12 is greater than the friction coefficient between the thin-film object 31 and the fingertips 11 and 12. However, depending on conditions such as the surface roughness or the materials used for the fingertips 11 and 12 and the thin-film object 31, the friction coefficient between the fingertips 11 and 12 can sometimes be smaller than the friction coefficient between the thin-film object 31 and the fingertips 11 and 12.

In detail, for example, in FIG. 4, it is assumed that the fingertips 11 and 12 are composed of silicon rubber and the thin-film object 31 is composed of a natural rubber film with, for example, a maximum stationary friction coefficient greater than that of silicon rubber. In this case, the maximum stationary friction coefficient $\mu_{S0}$ of thin-film object and the maximum stationary friction coefficient $\mu_{T0}$ between fingertips have a relationship expressed by the following expression (12):

$$\mu_{S0} > \mu_{T0} \quad (12)$$

Therefore, when a shearing force $f_T$ with a magnitude that still does not cause the fingertips 11 and 12 to start sliding against the thin-film object 31 is applied, the fingertips 11 and 12 may sometimes start to slide relatively with respect to each other.

Figure 12:
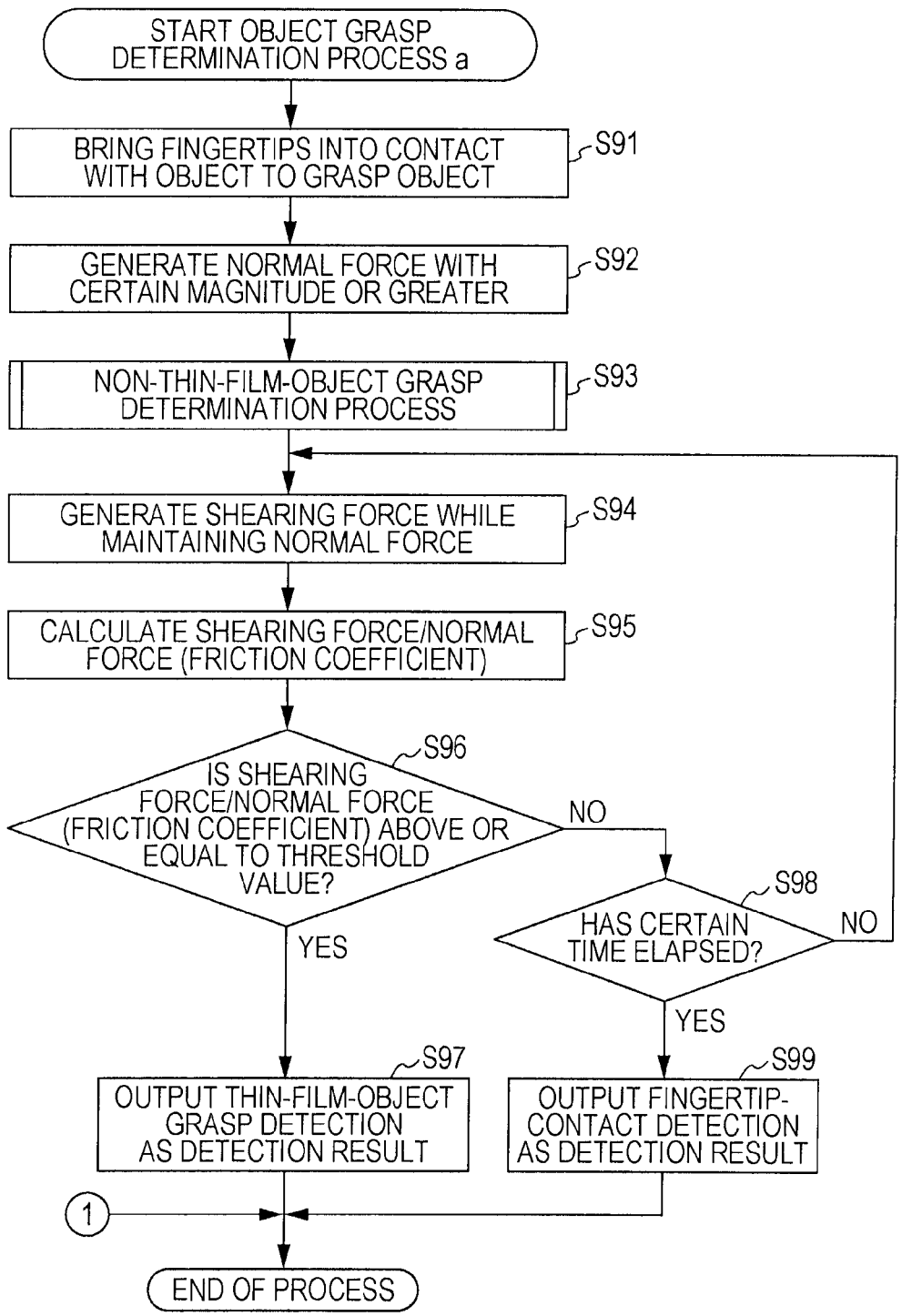
Figure 13:
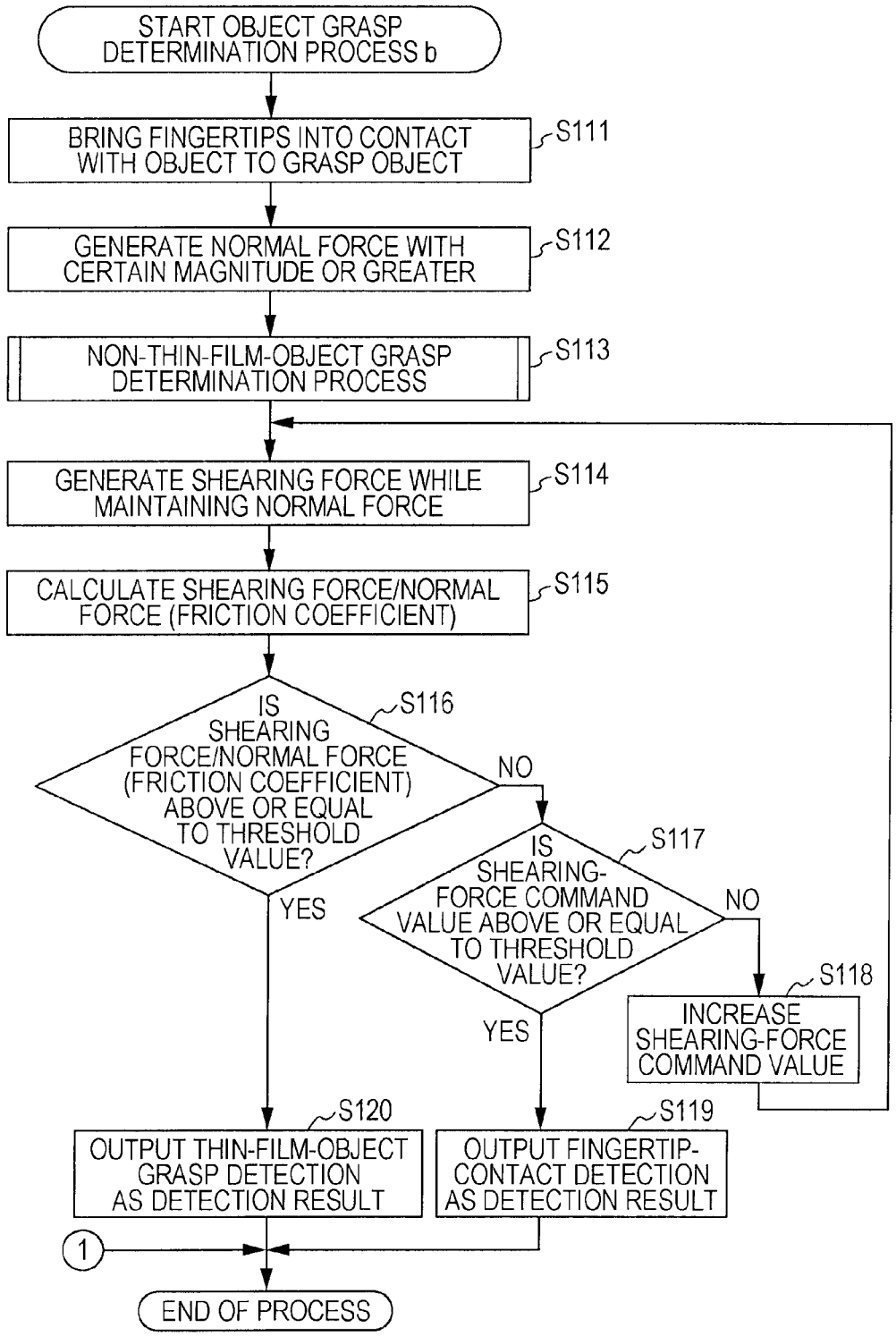
FIG. 13 is a flow chart illustrating an object grasp determination process b.
Figure 14:
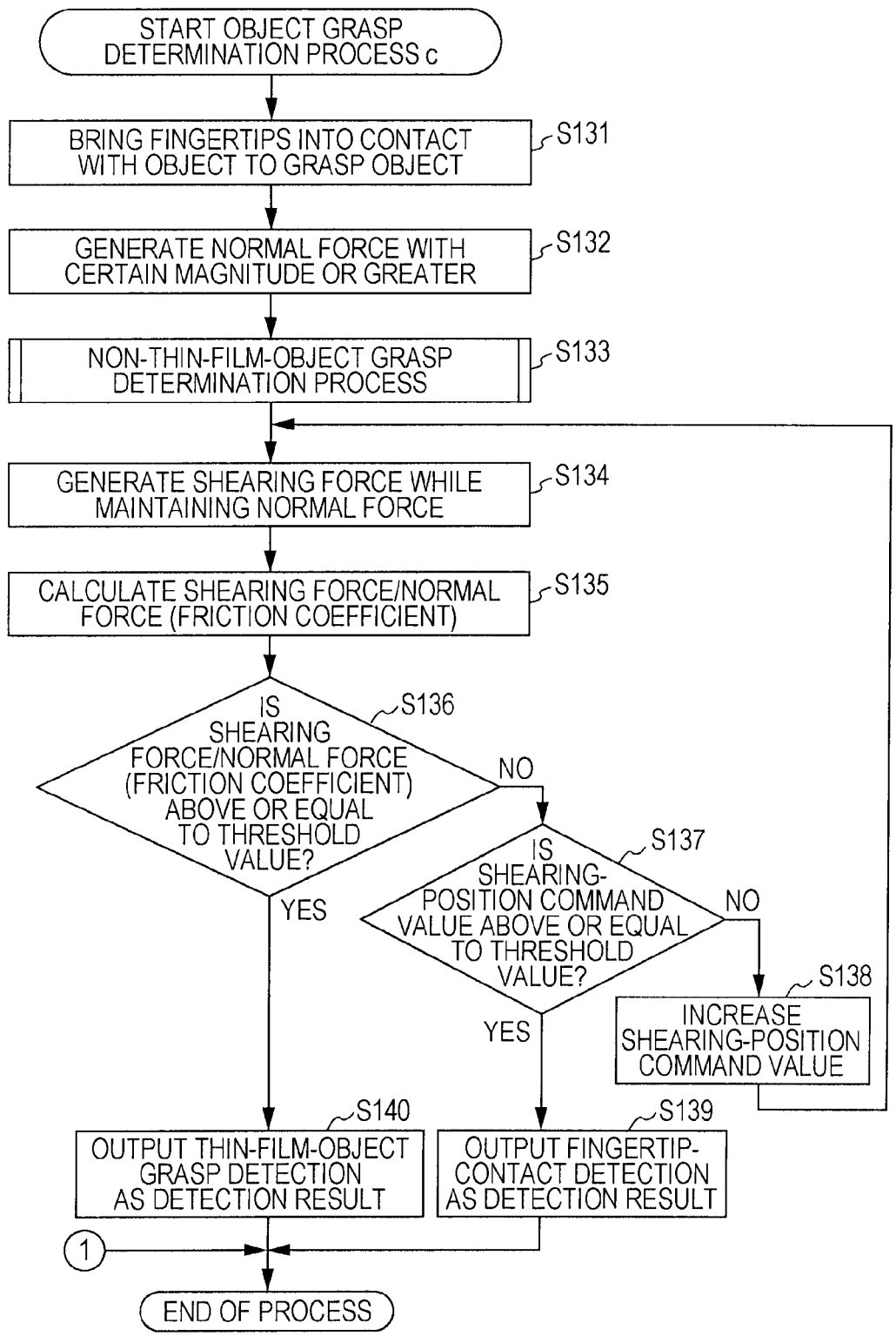
FIG. 14 is a flow chart illustrating an object grasp determination process c.

In this case, an object grasp determination process a shown in FIG. 12 may be used in place of the object grasp determination process A in FIG. 6, an object grasp determination process b shown in FIG. 13 may be used in place of the object grasp determination process B in FIG. 8, and an object grasp determination process c shown in FIG. 14 may be used in place of the object grasp determination process in FIG. 11.

Regardless of which object grasp determination process is used, the process is substantially the same except for the fact that the final result (detection result) prior to the end of the process is inverted.

Specifically, step S11 to steps S16 and S18 in FIG. 6 are basically the same as step S91 to steps S96 and 98 in FIG. 12. The detection results obtained from step S17 and step S19 in FIG. 6 are the opposite of the detection results obtained from step S97 and step S99 in FIG. 12.

Step S51 to step S58 in FIG. 8 are basically the same as step S111 to step S118 in FIG. 13. The detection results obtained from step S60 and step S59 in FIG. 8 are the opposite of the detection results obtained from step S120 and step S119 in FIG. 13.

Step S71 to step S78 in FIG. 11 are basically the same as step S131 to step S138 in FIG. 14. The detection results obtained from step S80 and step S79 in FIG. 11 are the opposite of the detection results obtained from step S140 and step S139 in FIG. 14.

To summarize the above description, when the maximum stationary friction coefficient $\mu_{S0}$ of thin-film object is smaller than the maximum stationary friction coefficient $\mu_{T0}$ between fingertips, the object grasp determination process A shown in FIG. 6, the object grasp determination process B shown in FIG. 8, or the object grasp determination process C shown in FIG. 11 may be used.

In contrast, when the maximum stationary friction coefficient $\mu_{SO}$ of thin-film object is greater than the maximum stationary friction coefficient $\mu_{TO}$ between fingertips, the object grasp determination process a shown in FIG. 12, the object grasp determination process b shown in FIG. 13, or the object grasp determination process c shown in FIG. 14 may be used.

By using a combination of the object grasp determination process A shown in FIG. 6 and the object grasp determination process a shown in FIG. 12, a combination of the object grasp determination process B shown in FIG. 8 and the object grasp determination process b shown in FIG. 13, or a combination of the object grasp determination process C shown in FIG. 11 and the object grasp determination process c shown in FIG. 14, the thin-film-object grasp detection and the fingertip-contact detection can be achieved regardless of the magnitude relationship between the maximum stationary friction coefficient $\mu_{SO}$ of thin-film object and the maximum stationary friction coefficient $\mu_{TO}$ between fingertips.

Figure 15:
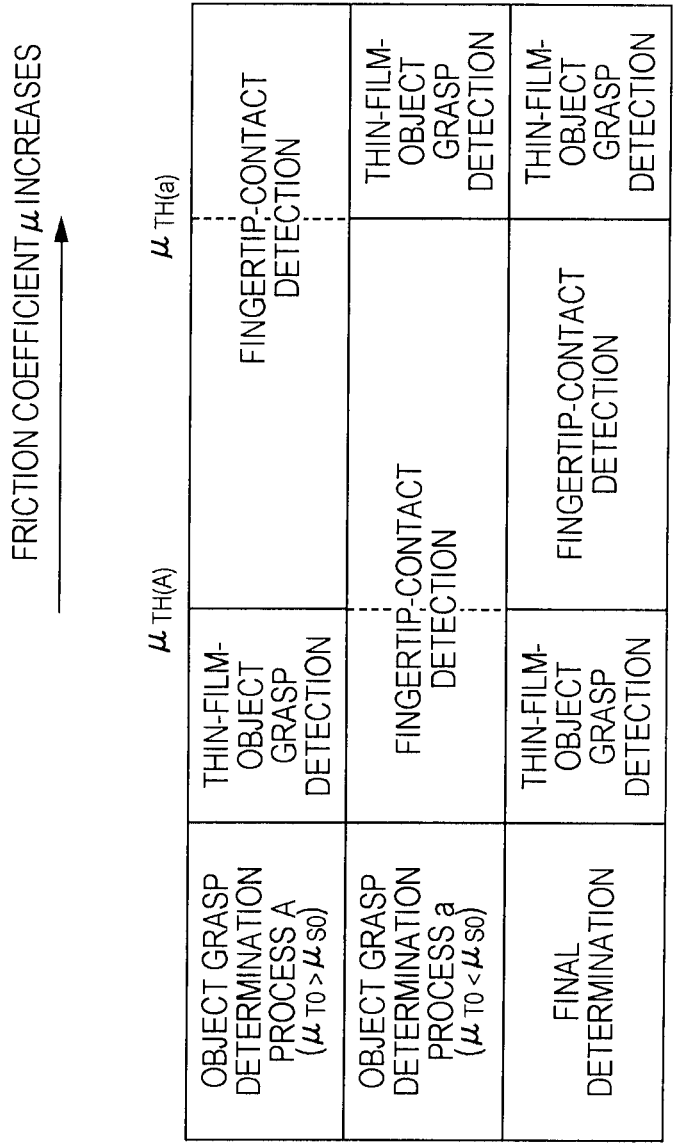
FIG. 15 is a diagram for explaining a combination of a plurality of object grasp determination processes.

FIG. 15 illustrates an algorithm for determining thin-film-object grasp detection and fingertip-contact detection when a combination of the object grasp determination process A and the object grasp determination process a is used (referred to as "object grasp determination technique" hereinafter).

In the object grasp determination process A ($\mu_{TO} > \mu_{SO}$), the thin-film-object detecting portion 59 detects that the thin-film object 31 is grasped if the friction coefficient is below a threshold value $\mu_{TH}(A)$ or detects that the fingertips 11 and 12 are in contact with each other, that is, an object is not grasped, if the friction coefficient is above or equal to the threshold value $\mu_{TH}(A)$.

In the object grasp determination process a ($\mu_{TO} < \mu_{SO}$), the thin-film-object detecting portion 59 detects that the fingertips 11 and 12 are in contact with each other if the friction coefficient is below a threshold value $\mu_{TH}(a)$ or detects that the thin-film object 31 is grasped if the friction coefficient is above or equal to the threshold value $\mu_{TH}(a)$.

By combining the object grasp determination process A and the object grasp determination process a, it can be determined that the fingertips 11 and 12 are in contact with each other when the friction coefficient is above or equal to the threshold value $\mu_{TH}(A)$ but below the threshold value $\mu_{TH}(a)$, or it can be determined that the thin-film object 31 is grasped when the friction coefficient is a value outside the above range.

The object grasp determination technique shown in FIG. 15 can be similarly used by combining the object grasp determination process B in FIG. 8 and the object grasp determination process b in FIG. 13 or by combining the object grasp determination process C in FIG. 11 and the object grasp determination process c in FIG. 14.

The above-described processes can each be executed using hardware or software.

Figure 16:
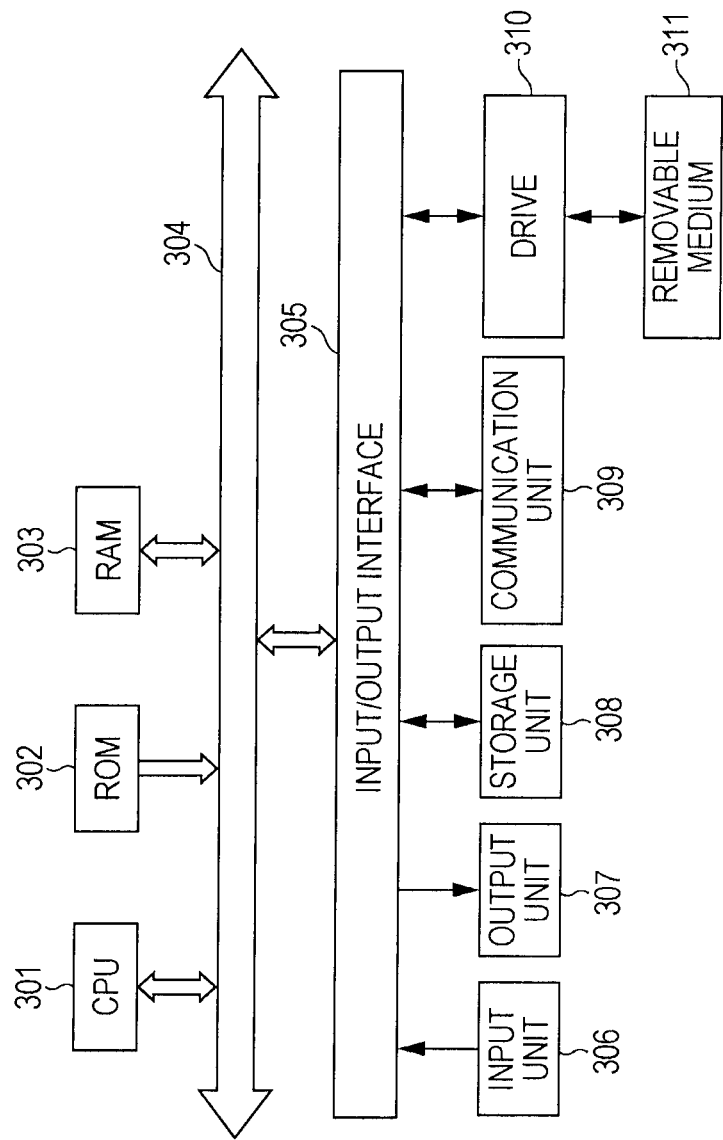
FIG. 16 is a block diagram illustrating a configuration example of a computer that is included in or controls the driving of a robot hand device according to an embodiment of the present invention.

If the above-described processes are to be executed using software, the control device according to an embodiment of the present invention can be configured to, for example, include a computer shown in FIG. 16. Alternatively, the robot hand device according to an embodiment of the present invention may be controlled by the computer shown in FIG. 16.

In FIG. 16, a central processing unit (CPU) 301 executes various processes in accordance with a program stored in a read-only memory (ROM) 302 or a program loaded into a random-access memory (RAM) 303 from a storage unit 308. The RAM 303 also appropriately stores, for example, data to be used by the CPU 301 for executing various processes.

The CPU 301, the ROM 302, and the RAM 303 are connected to each other via a bus 304. The bus 304 is also connected to an input/output interface 305.

The input/output interface 305 is connected to an input unit 306 including, for example, a keyboard and a mouse, an output unit 307 including, for example, a display, the storage unit 308 including, for example, a hard disk, and a communication unit 309 including, for example, a modem and a terminal adapter. The communication unit 309 controls communication performed with other devices (not shown) via a network including the Internet.

The input/output interface 305 is connected to a drive 310 where necessary. A removable medium 311 defined by, for example, a magnetic disk, an optical disk, a magneto-optical disk, or a semiconductor memory is fitted in the input/output interface 305. Where necessary, a computer program read out from the removable medium 311 is installed in the storage unit 308.

In order to execute a process using software, a program included in the software is installed, via a network or from a storage medium, into a computer that is built in designated hardware or into, for example, a general personal computer capable of executing various functions by installing various programs therein.

As shown in FIG. 16, a storage medium containing such a program may be distributed as a separate component from the device body to provide the program to a user, and may be defined by the removable medium (packaged medium) 311 that may include a magnetic disk (including a floppy disk), an optical disk (including a compact disk read-only memory (CD-ROM) and a digital versatile disk (DVD)), a magneto-optical disk (including a mini disk (MD)), or a semiconductor disk. Alternatively, the storage medium may be provided to the user in a pre-built-in state in the device body, and may be defined by the ROM 302 having the program stored therein or by the hard disk included in the storage unit 308.

In this specification, the steps written in the program stored in the storage medium may be performed in a time-series fashion in the written order, but do not necessarily have to be performed in a time-series fashion. Alternatively, the steps may be performed in a parallel fashion or in an individual fashion.

In this specification, the term "system" is used to indicate an entire device constituted by a plurality of devices or processing units.

The present application contains subject matter related to that disclosed in Japanese Priority Patent Application JP 2008-295360 filed in the Japan Patent Office on Nov. 19, 2008, the entire content of which is hereby incorporated by reference.

It should be understood by those skilled in the art that various modifications, combinations, sub-combinations and alterations may occur depending on design requirements and other factors insofar as they are within the scope of the appended claims or the equivalents thereof.

What is claimed is:
1. A control device comprising:
a force detector configured to detect a force in a normal direction and a force in a shearing direction of fingertips of a robot hand device respectively as a normal force and a shearing force; and
an object detector configured to calculate a friction coefficient using the normal force and the shearing force detected by the force detector and for detecting whether or not a thin-film object having a maximum friction coefficient different from a maximum stationary friction coefficient between the fingertips is grasped between the fingertips on the basis of the calculation result.

2. The control device according to claim 1, further comprising a position detector configured to detect a position of the fingertips, wherein the object detector further detects whether or not a non-thin-film object thicker than the thin-film object is grasped between the fingertips on the basis of the detection result of the position detecting means, wherein if the detection result indicates that the non-thin-film object is grasped between the fingertips, the object detector prohibits the detection of whether or not the thin-film object is grasped between the fingertips, and wherein if the detection result indicates that the non-thin-film object is not grasped between the fingertips, the object detector commences the detection of whether or not the thin-film object is grasped between the fingertips.

3. The control device according to claim 1, wherein the object detector compares a threshold value preliminarily determined from the maximum stationary friction coefficient between the fingertips with the friction coefficient and detects whether or not the thin-film object is grasped between the fingertips on the basis of the comparison result.

4. A control method comprising the steps of:

detecting, using a force detector, a force in a normal direction and a force in a shearing direction of fingertips of a robot hand device respectively as a normal force and a shearing force; and calculating, using an object detector, a friction coefficient using the detected normal force and the detected shearing force and to detect whether or not a thin-film object having a maximum friction coefficient different from a maximum stationary friction coefficient between the fingertips is grasped between the fingertips on the basis of the calculation result.

5. A non-transitory, computer-readable medium comprising instructions for executing a control process that includes the steps of:

causing a computer to detect a force in a normal direction and a force in a shearing direction of fingertips of a robot hand device respectively as a normal force and a shearing force; and causing the computer to calculate a friction coefficient using the detected normal force and the detected shearing force and to detect whether or not a thin-film object having a maximum friction coefficient different from a maximum stationary friction coefficient between the fingertips is grasped between the fingertips on the basis of the calculation result.

* * * * *